United States Patent [19]

Mirviss et al.

[11] Patent Number: 4,613,691
[45] Date of Patent: Sep. 23, 1986

[54] PREPARATION OF AMINO ACIDS FROM UNSATURATED HYDANTOINS

[75] Inventors: Stanley B. Mirviss, Stamford, Conn.; Mark W. Empie, Ashland, Mass.

[73] Assignee: Stauffer Chemical Company, Westport, Conn.

[21] Appl. No.: 751,581

[22] Filed: Jul. 8, 1985

Related U.S. Application Data

[63] Continuation-in-part of Ser. No. 642,238, Aug. 17, 1984, abandoned.

[51] Int. Cl.$^4$ ............................................. C07C 99/08
[52] U.S. Cl. .................................... 562/443; 562/401; 562/445; 562/446; 562/447; 562/449; 562/426; 562/575; 562/567; 562/574; 562/507; 562/556; 562/561; 562/564; 558/414
[58] Field of Search ............... 562/443, 444, 445, 446, 562/401, 447, 449, 426, 575, 567, 574, 505, 556, 561, 504; 260/465 E

[56] References Cited

U.S. PATENT DOCUMENTS

| | | | |
|---|---|---|---|
| 2,435,399 | 2/1948 | Livak et al. | 562/442 |
| 2,479,065 | 8/1949 | Gresham | 562/442 |
| 2,557,920 | 6/1951 | White | 562/444 |
| 2,642,459 | 8/1951 | White | 562/444 |
| 3,668,221 | 6/1972 | Shima et al. | 562/443 |
| 3,790,599 | 2/1974 | Zundel | 562/443 |
| 3,813,317 | 5/1974 | Benolton et al. | 562/444 |
| 3,832,388 | 8/1974 | Loreny | 562/444 |
| 3,847,933 | 11/1974 | Tyler | 562/443 |
| 3,878,043 | 4/1975 | Matta et al. | 562/443 |
| 4,262,092 | 4/1981 | Bauer | 562/442 |

FOREIGN PATENT DOCUMENTS

| | | | |
|---|---|---|---|
| 0089886 | 3/1983 | European Pat. Off. | 562/444 |
| 1518339 | 12/1964 | Fed. Rep. of Germany | 562/444 |
| 1240638 | 7/1971 | United Kingdom | 562/442 |

OTHER PUBLICATIONS

Boyd et al, Biochem. J., vol. 29, pp. 542–545 (1933).
Harn et al., J. A. Swu. Chem. Soc., vol. 45, pp. 843–847 (1923).
Bucherer, J. Prakt: Chemie Band 141, pp. 30–43 (1934).
Toi, vol. 36, #6, pp. 739–743 (1963).
Wretland, J. Biol. Chem., vol. 186, pp. 221–224 (1950).
Pugniere et al, Biotech Letters, vol. 5, pp. 447–452 (1983).
Yamada et al, J. Org. Chem., vol. 48, pp. 843–846 (1983).
Barrows, J.A.C.S., vol., pp. 185–190 (1949).

*Primary Examiner*—James H. Reamer
*Attorney, Agent, or Firm*—Paul J. Juettner

[57] ABSTRACT

Amino acids can be easily prepared by reducing unsaturated hydantoins to the corresponding saturated hydantoins by hydrogenating the unsaturated hydantoin using either Raney Nickel catalyst in the presence of more than a stoichiometric amount of caustic or by using zinc and hydrochloric acid followed by hydrolyzing the resultant composition with at least 3 molar equivalents of an alkali metal hydroxide to produce a racemate of an alpha amino acid. The amino acid in suitable derivative form can then be resolved particularly using a two-phase solvent system. The residual isomer of the amino acid remaining after the resolution process can then be racemized using either pyridoxal-5-phosphate or an aliphatic acid in combination with an aldehyde or a ketone. By these procedures, it is possible to obtain high yields of amino acids.

43 Claims, No Drawings

PREPARATION OF AMINO ACIDS FROM UNSATURATED HYDANTOINS

This application is a continuation-in-part of application Ser. No. 642,238, filed Aug. 17, 1984 now abandoned, titled "Preparation of Amino Acids From Unsaturated Hydantoins".

FIELD OF THE INVENTION

The present invention relates to a novel process for preparing amino acids from unsaturated hydantoins. More particularly, this invention relates to a novel process for the preparation of amino acids by hydrogenating unsaturated hydantoins using inexpensive catalysts followed by hydrolysis of that product to the corresponding amino acid. The racemic mixture of amino acids thus produced can be resolved using a stereospecific enzyme in a two phase water immiscible organic solvent/water system. The present invention also relates to a process for racemizing the residual amino acid isomer from the resolution process. The process does not require high pressure, can be carried out in aqueous solvents, and results in substantially complete conversion of the unsaturated hydantoin in short reaction times using low levels of catalyst to amino acids.

BACKGROUND OF THE INVENTION

It has long been common practice to use hydantoin and substituted hydantoins are precursors and intermediates in the synthesis of amino acids. The use of substituted hydantoins in the synthesis of amino acids such as alanine, methionine, tryptophan and lysine is well documented in the prior art. (Kirk Othmer, Encyclopedia of Chemical Technology, Volume 12, pages 694–695). These unsaturated hydantoins can be formed by any number of reactions with one of the more commonly used being a condensation reaction between an aldehyde and a substituted or unsubstituted hydantoin. In this reaction, an ethylenic bond is formed between the non-carbonyl, or C-5, carbon of the hydantoin moiety and the carbonyl carbon of the original aldehyde. Further reduction, or hydrogenation, of this ethylenic linkage is a necessary step in the synthesis of some amino acids. This step must be done without hydrogenation of any of the aromatic or aliphatic substituents of the hydantoin moiety other than at this ethylenic linkage. Previously, this hydrogenation step has been done using hydrogen and a nickel catalyst under high pressure or by using hydrogen and a very expensive noble metal catalyst such as palladium or platinum under little or no pressure.

The use of one or more of these techniques is reported in a number of U.S. patents. In U.S. Pat. No. 2,605,282, 5-vanillylidenehydantoin is reduced to the 5-vanillylhydantoin by dissolving the unsaturated hydantoin in an aqueous solution containing 4 to 10 percent by weight of sodium hydroxide (75 mole % of the unsaturated hydantoin) and shaking the mixture with hydrogen under pressure in the presence of a palladium containing hydrogenation catalyst. The reduction is carried out at a temperature of 25° to 40° C. at a pressure of 60 pounds per square-inch gauge or higher for 1 to 4 hours.

In U.S. Pat. No. 2,479,065, 5-benzalhydantoin is reduced to 5-benzylhydantoin using a caustic activated nickel aluminum alloy catalyst, methanol as a solvent and pressures of from 750 to 760 atmospheres. One disadvantage of the above method is the use of extremely high pressures to complete the hydrogenation in a short reaction time. The above mentioned patent does not specifically define the type of nickel aluminum alloy to be caustic activated or the degree of caustic activation. Although nickel aluminum alloys are commonly employed catalysts in hydrogenation procedures, a distinction must be drawn between a nickel alloy catalyst and a particular class of nickel type catalyst called Raney Nickel catalyst. The accepted method of making the latter catalyst involves reacting the nickel-aluminum alloy with caustic to remove the aluminum and then washing the precipitated nickel with water to remove essentially all the caustic to produce a spongy nickel catalyst. [Ind. and Eng. Chem. 33 1199 (1940)]: Hereinafter, the term Raney Nickel catalyst refers to the form of nickel catalyst produced by the above procedure.

SUMMARY OF THE INVENTION

In accordance with the present invention, amino acids can be easily prepared by reducing unsaturated hydantoins to the corresponding saturated hydantoins by hydrogenating the unsaturated hydantoin using either Raney Nickel catalyst in the presence of more than a stoichiometric amount of caustic or by using Zinc and hydrochloric acid followed by hydrolyzing the resultant composition with at least 3 molar equivalents of an alkali metal hydroxide to produce a racemate of an alpha amino acid. The racemate of the amino acid can then be resolved using a stereospecific enzyme in a two phase water immiscible organic solvent/water system. The residual amino acid isomer from the resolution process can then be racemized using either pyridoxal-5-phosphate or an aliphatic acid in combination with an aldehyde or a ketone. Using this method, it is possible to obtain high yields of the desired amino acid in short reaction times using low levels of catalyst.

DETAILED DESCRIPTION OF THE INVENTION

The process of the invention is directed to the production of amino acids from unsaturated hydantoins of the general formula.

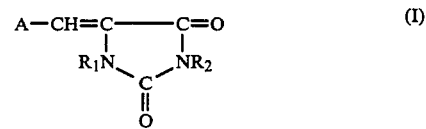

where A is X or Y, and X is an unbranched or branched alkyl or alkenyl group, a cycloalkyl group, a cycloalkenyl group, an alkylthio group, a haloalkyl group, a haloalkenyl group, a hydroxyalkyl group, an aralkyl group, a mono- or dialkylaminoalkyl group, an acylaminoalkyl group, or a mercaptoalkyl group. Preferably the alkyl groups contain 1 to about 20, especially 1 to about 10 carbon atoms, the alkenyl group 2 to about 10, especially 2 to about 5 carbon atoms, the cycloalkyl and cycloalkenyl groups from about 3 to about 15, preferably from about 3 to about 10 carbon atoms. In a given case in the cycloalkyl or cycloalkenyl group, one or more —CH$_2$— units can also be replaced by —O—, —S—, or —NH—, or —C= can be replaced by —N— so that there is present the corresponding heterocyclic ring with 3 to about 15, preferably from about 3 to about 10 ring atoms. The alkoxy, alkylthio, hydroxyalkyl, mercaptoalkyl, mono- or dialkylaminoalkyl and acylaminoalkyl groups contain preferably 1 to about 10, especially 1 to about 6 carbon atoms in the alkyl or acyl groups, and Y is

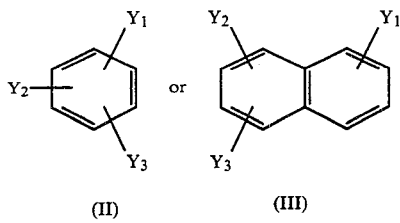

(II) (III)

in which $Y_1$, $Y_2$, and $Y_3$ are the same or different and can be X as defined above, hydrogen, halogen, e.g. of atomic weight 9 to 80, a hydroxy group, a nitro group, a cyano group, an amino group, an aralkyl group, or an alkaryl group. Preferably, the aralkyl and the alkaryl groups contain from about 7 to about 15 carbons in the alkylene or alkyl groups. In a given case, two of the groups $Y_1$ to $Y_3$ together can form an alkylene or alkenylene group with from about 3 to about 5 carbon atoms whereby in this case one or more —$CH_2$— units can be replaced by —O—, —S—, or —NH— or —CH= can be replaced by —N=.

$R_1$ and $R_2$ are the same or different and are hydrogen, alkyl, aryl, or amino.

The unsaturated hydantoin can be purchased commercially or can be synthesized, for example, through the condensation reaction of an aliphatic or aromatic aldehyde with a substituted or unsubstituted hydantoin.

One such condensation reaction is disclosed in the copending application of S. Mirviss. Ser. No. 641,888, filed Aug. 17, 1984, entitled "New Inexpensive Catalyst for the Production of Unsaturated Hydantoins", the subject matter of which is incorporated herein by reference. In this application, the condensation reaction of an aldehyde and hydantoin is carried out in the presence of a basic salt of an inorganic acid. In this process, there are employed aliphatic aldehydes having the formula

X—CHO wherein X is as defined above. Representative aldehydes include butyraldehyde, isobutyraldehyde, valeraldehyde, isovaleraldehyde, caproaldehyde, enanthaldehyde, nonaldehyde, cyclobutylaldehyde, cyclopentylaldehyde, cyclohexylaldehyde, furfural, 2-thiophenealdehyde, 2-pyrrolealdehyde, imidazolealdehyde, oxazolealdehyde, 3-indolealdehyde, pyridylaldehyde, pyrimidylaldehyde, malonic acid half aldehyde and monoaldehyde derivatives of decarboxylic acids.

Appropriate aromatic aldehydes having the formula Y—CHO include benzaldehyde, tolylaldehyde, 4-isopropylbenzaldehyde, 4-hydroxybenzaldehyde, 3,4,5-trimethoxybenzaldehyde, 3-bromo-4-methoxybenzaldehyde, 3,4-methylenedioxybenzaldehyde, 2-hydroxy-4-nitrobenzaldehyde, 4,5-dimethoxy-2-nitrobenzaldehyde, salicylaldehyde, vanillin, 4-phenylbenzaldehyde, 4-benzylbenzaldehyde, 4-fluorobenzaldehyde, 4-dimethylaminobenzaldehyde, 4-acetoxybenzaldehyde, 4-acetaminobenzaldehyde, 4-methylthiobenzaldehyde, and 3,5-dichloro-4-hydroxybenzaldehyde. Additional aldehydes include p-tolylaldehyde, m-tolylaldehyde, 4-chlorobenzaldehyde, 4-hexylbenzaldehyde, 2-allylbenzaldehyde, 4-allylbenzaldehyde, 2-vinylbenzaldehyde, 3-vinylbenzaldehyde, 4-methallylbenzaldehyde, 4-crotylbenzaldehyde, 2-nitrobenzaldehyde, 3-nitrobenzaldehyde, 4-nitrobenzaldehyde, 2-aminobenzaldehyde, 4-aminobenzaldehyde, 4-cyclopropylbenzaldehyde, 2-cyclopropylbenzaldehyde, 4-cyclohexylbenzaldehyde, 2,6-dichlorobenzaldehyde, anisaldehyde, 3-hydroxybenzaldehyde, 2-hydroxybenzaldehyde, 2-hydroxy-4-methylbenzaldehyde, 2-hydroxy-3-methoxybenzaldehyde, veratraldehyde, 2,4-dihydroxybenzaldehyde, 2,5-dihydroxybenzaldehyde, 4-cyclohexenylbenzaldehyde, 4-cyclooctylbenzaldehyde, 4-piperidinylbenzaldehyde, 4-pyridylbenzaldehyde, 4-furylbenzaldehyde, 4-thienylbenzaldehyde, 4-phenylethylbenzaldehyde, 4-sec.butylbenzaldehyde, 4-morpholinobenzaldehyde, 4-isopropoxybenzalidehyde, 2-propoxybenzaldehyde, 3-ethoxybenzaldehyde, 4-hexoxybenzaldehyde, 2-isopropylaminobenzaldehyde, 4-hexylaminobenzaldehyde, 4-diethylaminobenzaldehyde, 4-dipropylaminobenzaldehyde, 4-methylethylaminobenzaldehyde, 3,4-ethylenedioxybenzaldehyde, 4-acetylthiobenzaldehyde, 4-propionoxybenzaldehyde, 4-formyloxybenzaldehyde, 4-butyroxybenzaldehyde, 3,4-tetramethylenebenzaldehyde, 3,4-trimethylenebenzaldehyde, 3,4-dihydroxybenzaldehyde, alpha napthaldehyde, beta naphthaldehyde, and 3-indenecarboxaldehyde.

In addition, hydantoins substituted at the N-1 or N-3 position can also be used in the condensation reaction. Examples of such hydantoins include, 3-methylhydantoin, 1,3-dimethylhydantoin, 1-phenylhydantoin, 3-benzylhydantoin, 1,3-dibenzylhydantoin and the like.

The inexpensive basic salts of an inorganic acid to be employed in the reaction include ammonium bicarbonate or ammonium carbonate with the bicarbonate being the preferred compound. The basic salt can be derived from any inorganic acid with a $pK_a$ of above 5. For example, basic salts derived from carbonic acid ($pK_a=10.3$), the bicarbonate of carbonic acid ($pK_a=6.4$), or the monoacid phosphate of phosphoric acid ($pK_a=12.4$) can be used.

The basic salt used is dissolved in an aqueous solvent. Other solvents include water/alcohol, or water/glycol(s). Preferably, the aldehyde is added to the solution of catalyst, solvent and hydantoin.

Generally, the condensation takes place at a temperature between about 0° to about 120° C., especially at a temperature of about 10° to about 105° C. The pressure at which the reaction is carried out is atmospheric but superatmospheric pressure can also be used.

The molar ratio of aldehyde to hydantoin can be 0.8 to 1.2. Generally, it is advantageous to employ per mole of hydantoin from about 0.85 to 1.15 moles, especially from about 0.9 to about 1.1 moles of the aldehyde.

Per mole of hydantoin, there is suitably employed an effective amount, ranging from at least 0.10 mole, preferably from about 0.20 to about 1.0 moles, especially from about 0.20 to about 0.6 moles, of the basic salt of the inorganic acid.

The reaction can be carried out on a small scale or a large scale and can be done batchwise or in a continuous fashion. If a continuous reaction is chosen, the reaction is monitored and reactants are added when depleted.

The unsaturated hydantoin as produced in the process of copending application Ser. No. 641,888, available commercially or produced through other names, can be rapidly reduced with little or no pressure to the corresponding saturated hydantoin or ring open derivative thereof by carrying out the hydrogentation of the unsaturated hydantoin using a Raney Nickel catalyst in the presence of more than a stoichiometric amount of caustic as described in copending application of S. Mirviss, Ser. No. 641,886, filed Aug. 17, 1984, entitled "Hydrogenation of Substituted, Unsaturated Hydantoins to Substituted, Saturated Hydantoins".

The Raney Nickel catalyst employed is available commercially (Davison Division of W. R. Grace). Briefly, the preparation of this catalyst involves fusing about 50 parts nickel with about 50 parts aluminum as described in U.S. Pat. Nos. 1,628,190 and 1,915,473, pulverizing the alloy and dissolving out most of the aluminum with sodium hydroxide solution [J. Am. Chem. Soc. 54, 4116 (1932)]. The nickel is then washed to remove any residual sodium hydroxyide [Ind. and Eng. Chem. 33 1199 (1940)]. The exact mechanism through which Raney Nickel exerts its catalytic activity is not known. Various theories have been put forth including absorbed hydrogen or the formation of a nickel hydride. A complete discussion of this subject can be found in Freifelder, *Practical Catalytic Hydrogenation*, Wiley Interscience, 1971, pp. 6–7, the discussion therein being incorporated by reference. As is known to those skilled in the art, the Raney Nickel catalyst must be kept under water.

The hydrogenation reaction of the present invention is carried out in the presence of an effective amount of Raney Nickel catalyst ranging from about 0.1 to about 50, preferably from about 0.3 to about 40 percent by weight of the unsaturated hydantoin. The unsaturated hydantoin is dissolved in an aqueous solvent such as water or an alcohol, with water the preferred medium, and an effective amount of solid or liquid caustic of any strength from 10–100% by weight, ranging from about 101 to about 300, preferably from about 105 to about 250, with optimum results at about 105 to about 200 mole percent, based on the amount of unsaturated hydantoin, is added to the reaction mixture. The strength of the caustic solution produced can range from 0.1 to 15 weight percent (0.1N–2.5N) based on the amount of water used. Preferably, the process would comprise using a reaction mixture containing from about 0.5 to about 10 weight percent sodium hydroxide. Other caustics, such as the hydroxy derivatives of lithium, potassium, etc. may also be used.

Hydrogen is bubbled in with vigorous stirring. The reaction can be performed at atmospheric or elevated pressures. The higher the pressure, the faster the reaction rate but preferably, the reaction is run at a pressure of 0 to about 100 psig.

The temperature at which the reaction is run can range from 0° to about 100° C., preferably from about 10° to about 65° C. with optimum results being seen at from about 25° C. to about 40° C. Too high a temperature causes hydrolysis of the benzahydantoin to phenylpyruvate before substantial hydrogenation is effected.

The vessel in which the reaction is carried out in the laboratory may be a round bottom flask, a pressure resistant glass bottle, a Parr pressure bottle, a resin flask (bottle), a Morton flask, etc. The reaction may be performed in a batch fashion or a continuous fashion.

When the reactants are introduced, the reaction can be summarized as follows:

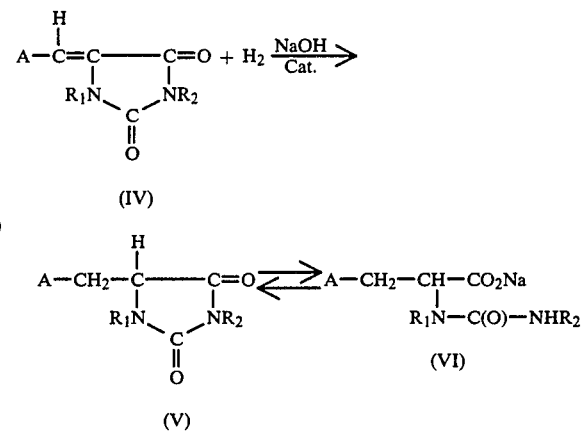

in which it is theorized that an equilibrium exists between compound (V), the saturated hydantoin, and compound (VI), the alkali metal, e.g. sodium, salt of the ring opened saturated hydantoin. Compound (VI) can also be called a sodium salt of an N-carbamyl, beta-substituted alanyl derivative. Either or both products are desirable since the process is designed to hydrogenate the ethylenic linkage between a methine carbon of the aliphatic, aromatic or heterocyclic substituent on the hydantoin moiety and the non-carbonyl carbon of the hydantoin moiety or its original derivative. Accordingly, the amount of either compound (V) and/or compound (VI) may be measured by conventional methods, including liquid chromatography, melting point, UV analysis, etc. Both compounds of formula (V) and formula (VI) can be hydrolyzed to the beta-substituted alanine.

An unsaturated hydantoin can also be reduced to the corresponding saturated hydantoin by carrying out the reduction in the presence of zinc plus hydrochloric acid. Through this method, almost complete reduction of the unsaturated hydantoin to the saturated form can be accomplished in short reaction times without the necessity of using hydrogen gas or pressure. This is disclosed in the copending application of S. Mirviss, Ser. No. 641,890, filed Aug. 17, 1984, entitled "Reduction of Unsaturated Hydantoins to Saturated Hydantoins".

The unsaturated hydantoin is dissolved and/or suspended in an appropriate solvent or diluent, with methanol being an example, although other solvents such as water, water/alcohol or water/glycol(s) may be used.

After the unsaturated hydantoin is added, the zinc and hydrochloric acid can be introduced in a variety of fashions. The zinc can be added first to the mixture containing the unsaturated hydantoin, and then the hydrochloric acid can be added over a period of time to the reaction mixture. Alternatively, the hydrochloric acid can be first added to the mixture containing the unsaturated hydantoin and then the zinc powder can be added over a period of time. In either case, after all the reactants have been added, the reaction is allowed to proceed for a period of time ranging from about 30 minutes to about 120 minutes to allow for complete reaction of the zinc and hydrochloric acid to take place. After this period, the reaction mixture is observed and if there is a quantity of zinc which remains unreacted, additional quantities of hydrochloric acid may be added to dissolve, or react with, the unreacted zinc.

Once all the added zinc is dissolved, the reaction is run for an additional period of time ranging from about 30 minutes to about 3 hours to allow for reaction completion.

The amount of zinc which is added to the reaction can range from about 100 to about 400 mole percent of zinc based on weight of the unsaturated hydantoin. The amount of hydrochloric acid added is based on the amount of zinc to be added. The amount of hydrochloric acid can range from about 200 to about 400 mole percent based on the amount of zinc added. The hydrochloric acid used is preferably concentrated hydrochloric acid containing over 30 weight percent HCl and concentrations ranging from 5 weight percent HCl to about 40 weight percent HCl can be used.

The zinc used can be in the form of a powder, or can be in any other form including filings, shavings, etc. The reaction may be carried out in any suitable vessel including round bottom flasks, Morton flasks, etc.

The temperature at which the reaction is run is preferably room temperature. During the course of the reaction, the temperature may rise but it is not necessary to do the reaction in an ice bath.

When all the reactants are present, the reaction may be summarized as per formulae (IV), (V) and (VI).

The saturated hydantoin or its ring opened derivatives including salt forms thereof are then hydrolyzed to the corresponding amino acids by any known procedure. The hydrolysis is preferably conducted using the process described in copending application of M. Empie, Ser. No. 642,293, filed Aug. 17, 1984, entitled "Process for the Synthesis of Amino Acids from Saturated Hydantoins", the subject matter of which is incorporated herein by reference. In accordance with this process, a saturated hydantoin or its ring opened derivatives including salt forms thereof can be effectively hydrolyzed by heating the same with an hydroxide of an alkali metal, preferably having an atomic number within the range of from 2 to 20, e.g., lithium, sodium and potassium hydroxides. The preferred hydroxide is sodium hydroxide. The hydroxide is used in an amount sufficient to provide at least about 3 and preferably at least about 5 molar equivalents based on the hydantoin or derivatives thereof. More preferably, the hydroxide is used in an amount ranging from about 3 to about 7 and most preferably from about 5 to about 7 molar equivalents. The amount of alkali used is based on a neutral (pH 6.5-7.5) solution of the hydantoin or its derivatives. If the original solution is highly basic, less hydroxide is needed to achieve the required level. If the original solution were highly acidic, more base would be required. The total amount of hydroxide used is determined as if the solution of hydantoin or derivatives is neutral.

The hydroxide must be used in an amount sufficient to provide about 1 molar equivalent for the reaction and 1-2 molar equivalents to neutralize the products of reaction, e.g., amino acid and $CO_2$. Preferably, and to obtain maximum hydrolysis in a minimum period of time, it is preferred that the molar equivalency of the hydroxide range from about 3 to about 6.

The addition sequence of hydroxide to hydantoin and derivatives is not critical. Sufficient agitation is needed to ensure uniform heating. The reaction vessel is preferably operated at atmospheric pressure though slight pressure of up to 3 atmospheres can be used to elevate heating temperature.

The hydrolysis reaction is conducted in an aqueous medium. The amount of water is sufficient to form an hydroxide solution having from about 12% to about 50% hydroxide solids. Water can be added to a mixture of a solution of hydroxide and the hydantoin or derivative to obtain the desired final percentage.

The aqueous solution is heated to a temperature within the range of from about 70° C. to about 110° C. as determined at atmospheric pressure. Generally, the reaction is conducted at reflux temperature. If additional heating is required above reflux, slight pressure can be used to elevate the reflux temperature. The temperature preferably ranges from about 90° C. to about 140° C. and more preferably from about 95° C. to about 105° C.

The reaction is conducted for a period of time sufficient to effect hydrolysis of at least about 70%. Preferably, the reaction is conducted for from about 4 to about 25 hours and more preferably from about 6 to about 20 hours. Hydrolysis yields of about 80% and even above 90% are obtainable.

At the conclusion of the reaction, the amino acid can be isolated from the reaction mixture and any salt formed during the reaction by appropriate means. In the case of phenylalanine, the amino acid can be precipitated from the reaction mixture by neutralizing the same. A majority of the salt will remain in the mother liquor. The precipitate can then be alcohol washed and toluene washed to remove a majority of the salt and any organic impurities. The phenylalanine can then be processed further by drying or further reaction. Other amino acids which cannot be precipitated by pH adjustment can be purified by other means known to a skilled artisan such as by ion exchange. The isolated product can be sold as such or as a purified amino acid, e.g., phenylalanine.

The amino acid so prepared is a racemate which must be converted to a form which can be resolved if a specific isomer is desired. Resolvable forms of the amino acids such as an amide or ester are those which are hydrolyzable by an enzyme capable of selectively forming an amino acid isomer of one optical rotation. The amino acid carbonyl can be substituted with a moiety hydrolyzable by an isomer selective enzyme. The amino nitrogen can also be modified with an enzyme hydrolyzable moiety. Both of these methods are well known to the skilled artisan. Preferably, the alpha amino nitrogen is underivatized (no covalent bonded moieties other than hydrogen) and the amino acid carbonyl is substituted with an enzyme hydrolyzable moiety. The preferred such moiety is the ester. Methyl and ethyl esters are most desirable though esters up to about 8 carbons can be used. Amino acids can be esterified by known methods including refluxing a solution of amino acid in methanol saturated with hydrogen chloride gas.

Carbonyl-substituted amino acids wherein the alpha amino nitrogen is underivatized can be represented by the formula:

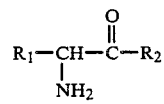

where $R_1$ can be straight or branched chain alkyl, alkylthio, alkoxy, benzyl and indolylalkyl and the hydroxy, halo, alkyl and nitro substituted derivatives thereof; $R_2$ is selected from the group consisting of $YR_3$, wherein Y is oxygen or sulfur, or $NHR_4$; $R_3$ can be straight or branched chain aliphatic radicals having from 1 to about 8 carbon atoms, aryl of up to 3 fused rings and the hydroxy, halo, alkyl and nitro substituted derivatives thereof and $R_4$ can be the same as defined in $R_3$ and hydrogen. As used herein the term alkyl used alone or in derivative form such as alkoxy, alkylthio, indolylalkyl and the like are intended to include groups ranging from 1 to about 8 carbon atoms. As used herein, the term "carbonyl-substituted" is intended to mean that the carbonyl group attached to the alpha carbon atom is substituted as is shown in the formula in this paragraph and halo includes fluoro, chloro, bromo and iodo.

Examples of the represented parent amino acids, i.e. as if $R_2$ were hydroxyl, include valine, leucine, isoleucine, methionine, phenylalanine (preferred), tyrosine, tryptophan, 3,4-dihydroxyphenylalanine, 2,4-dihydroxyphenylalanine; 3,4-methylenedioxyphenylalanine, 3,4-dimethoxyphenylalanine; 3(4)-methoxy-4(3)-hydroxyphenylalanine, 3,4-isopropylidenedioxyphenylalanine, 3,4-cyclohexylidenedioxyphenylalanine, 5-hydroxytryptophan, 5-methyltryptophan and 3,4,5-trihydroxyphenylalanine.

The moiety attached to the carbonyl group of the amino acid must be hydrolyzable by an enzyme to form the corresponding optical isomer of the free amino acid. The hydrolyzable group must not be of sufficient molecular weight or structure to cause the amino acid modified with the group to become completely insoluble in the water in which the hydrolysis must occur. Some of the groups which are included in the term "hydrolyzable" include the preferred ester, as well as amides and substituted amides ($R_2$ can be —$NH_2$, —NHR and NRR' wherein R' and R are the same or different and are the same as $R_1$) and thioesters (Y=S). The ester groups can be straight or branched chain aliphatic of from $C_1$ to $C_8$, aromatic up to three fused rings and substituted derivatives thereof such as halo, hydroxy, alkyl, nitro and the like. The amides are preferably prepared from straight or branched chain aliphatic amines of from $C_1$ to $C_8$, aryl of up to 3 fused rings and the alkyl, halo, hydroxy and nitro substituted derivatives thereof.

The problems inherent in the resolution of racemates of carbonyl-substituted amino acids can be overcome by contacting a solvent sulution of the carbonyl-substituted amino acid racemate dissolved in a substantially water-immiscible organic material with water; and, while portions of the so formed organic phase and aqueous phase are in contact, selectively hydrolyzing in at least a portion of the aqueous phase one of the isomers of the racemate with an enzyme capable of selectively hydrolyzing that optical isomer to the corresponding amino acid otpical isomer. The desired amino acid can be recovered by known techniques such as by precipitation from the aqueous solution.

By using the two phase solvent system, the requirement for continuous neutralization and the problems of enzyme activity inhibition such as caused by the buildup of the unresolved isomer and peptide formation can be avoided. This resolution system is disclosed in copending application of M. Empie Ser. No. 641,887, filed Aug. 17, 1984, entitled "Resolution of Racemates of Amino Acids", the context of which is incorporated herein by reference.

Preferably, the amino acid is phenylalanine or ring substituted derivatives thereof, i.e. hydroxy, alkyl, halo and nitro groups. The remaining description of the invention will be discussed in connection with the preferred amino acid, phenylalanine and its esters, though the teachings apply equally to the other named amino acids and hydrolyzable derivatives.

The racemate of carbonyl-substituted phenylalanine is dissolved in a substantially water-immiscible inert organic material which is a solvent for the racemate but is not a solvent for the corresponding amino acid. By immiscible it is intended to mean that the organic material is miscible in the water up to no more that 15% under the conditions of reaction. The organic material can be any water-immiscible or partially miscible organic solvent which is non-reactive with the carbonyl-substituted amino acid, the amino acid, the hydrolytic enzyme or has substantially no inhibitory effect on the enzyme activity. The organic solvents can be illustrated by toluene, methylene chloride, cyclohexanone, ethyl acetate, butyl acetate, butanol, and the like, with toluene being preferred. The carbonyl-substituted amino acid also can act as the solvent itself. The solvent to water volume ratio can range from about 1:10 to about 10:1 with a ratio of from about 2:1 to about 1:2 being preferred. The carbonyl-substituted amino acid, e.g. phenylalanine ester, content of the organic solvent can range from about 100% to about 5%, with from about 30% to about 10% on a weight per volume basis being preferred.

Carbonyl-substituted amino acids can also be used in the form of an inorganic salt. The inorganic salts can be specifically prepared or be the result of other processing such as racemization. The racemate is extracted into the immiscible organic material by neutralizing the salt with a sufficient amount of base such as sodium hydroxide, sodium bicarbonate, ammonia or sodium carbonate. The aqueous phase remaining which contains an inorganic salt can be removed or used as the aqueous phase for the enzyme hydrolysis. It is essential to the operation of the process of the invention that a substantial portion of the non-hydrolyzable isomer remain essentially in the organic phase during hydrolysis. Thus the non-hydrolyzed isomer of the racemate, which acts as an inhibitor to the esterase (protease) enzyme can be kept isolated from the enzyme while the hydrolysis reaction is proceeding. By "neutralized" is meant a pH within the range of from about 5.0 to about 8.0.

Following extraction, an enzyme which can selectively hydrolyze the carbonyl-substituted amino acid to the corresponding amino acid, e.g. an esterase (protease), is added to the aqueous phase. The enzyme can be selected to resolve i.e. hydrolyze, either the D or the L forms as desired but must be specific to one in order for the resolution to be effected. Proteases will hydrolyze the ester, amide or thioester substituted amino acids listed hereinbefore. The protease include chymotrypsin (in all forms), fungal protease, pancreatic extracts such as pancreatin, papain, subtilisin as well as commercially available enzymes such as Pronase TM brand and yeast protease. One of the preferred enzymes for converting the ester of L-phenylalanine into its corresponding amino acid is chymotrypsin. As is obvious to a skilled artisan, care should be taken to avoid excess loss of enzyme activity due to the use of reaction conditions which can adversely effect enzyme activity.

The enzyme can be added free or immobilized on a matrix or contained in an insolubilized enzyme column. In the case of a system utilizing the organic material and the aqueous phase in a single reactor, the enzyme can be added to the aqueous phase and the hydrolysis reaction allowed to proceed in that fashion. The enzyme could also be added in an immobilized state by stirring or suspending the immobilized enzyme in the aqueous portion of the reactor. The aqueous phase can also be pumped through an immobilized enzyme either contained totally within the aqueous phase or preferaby external to the reactor. In one preferred form of the present invention, portions of the aqueous phase are pumped out of the reaction vessel, through a filter to remove any solids, into the enzyme column where the hydrolysis reaction occurs followed by pumping the effluent from the column back through the organic phase and the aqueous phase. Any insoluble amino acid formed by the hydrolysis reaction can then be separated from the aqueous phase, preferably at the filter. Part of the aqueous phase remains in contact with the solvent phase to replenish the unresolved carbonyl-substituted amino acid.

In another embodiment, immobilized enzyme is suspended in the aqueous phase and the hydrolysis reaction is then conducted while the aqueous phase is in contact with the organic phase under the appropriate conditions for enzymatic hydrolysis. After the hydrolysis reaction has proceeded to the desired end point, the aqueous phase is separated from the organic phase, the immobilized enzyme is separated, and the desired amino acid isomer isolated from the aqueous phase by normal methods, such as by crystallization at temperatures appropriate for the amino acid isomer to be separated, such as from about 0° C. to about 10° C. and preferably from about 2° C. to about 6° C., for L-phenylalanine. To prevent the immobilized enzyme from becoming inactivated by blocking the pores on the support with precipitated amino acid, the concentration of amino acid is at or below the limits of solubility at the reaction conditions used.

The immobilized enzyme can be carried on any one of a number of supports well known to the prior art such as polymers of acrylic acid, or styrene crosslinked with divinyl benzene, or other supports such as wood, charcoal, glass, aluminum, silica, cellulose, starch, polyethylene terephthalate, agarose or dextran. The enzyme to substrate ratio can be within the range of from about 1:10 to about 1:10000 with a ratio of from about 1:2000 being preferred. Preferably, the enzyme is used in an amount sufficient to hydrolyze one of the optical isomers of the carbonyl-substituted racemate (50% of the total) in the two phase system to the corresponding amino acid within 3 hours.

The temperature and pH conditions within the aqueous phase or within the immobilized enzyme column are maintained under such conditions as to be favorable to the hydrolysis reaction with the enzyme being used. In connection with enzymes in general and chymotrypsin in particular, the temperature of reaction can range from about 0° C. to about 60° C. with from about 18° C. to about 50° C. being preferred. The pH of the reaction system can range from about 5 to about 8 with a preferred pH ranging from about 6.0 to about 7.5. Other conditions would be obvious to a skilled artisan depending on the enzyme utilized.

As the resolution reaction proceeds, the protease hydrolyzes the carbonyl-substituted amino acid, e.g. the L-phenylalanine ester, in the aqueous phase to the L-amino acid, e.g. L-phenylalanine. An equilibrium between the organic phase, which contains a majority of the racemate and the aqueous phase, which contains a small part of the racemate, is thus upset by the reduction of the isomer being hydrolyzed. To reestablish the equilibrum, the amino acid ester being hydrolyzed is partitioned from the organic phase into the aqueous phase. In this manner, the isomeric amino acid ester which is to be hydrolyzed is continuously drawn from the organic phase into the aqueous phase until substantially all of that isomer is hydrolyzed. While both isomers go from organic to aqueous only one returns to the organic layer unchanged while the other isomer is hydrolyzed. Thus the unhydrolyzed isomeric amino acid ester remains essentially in the organic layer so that the concentration of the unhydrolyzed isomer in the aqueous layer is kept constantly low so concentrations of the inhibiting isomer in the aqueous phase do not build up. In the course of partitioning the one isomer from the other isomer from the organic phase to the aqueous phase, the free amino group is protonated. This provides a buffering action needed to neutralize the acid produced from the ester hydrolysis. The free amino group absorbs a hydrogen ion, keeping the pH of the aqueous phase essentially constant without having to add an external neutralizing agent though an external weak neutralizing agent could be added if desired.

The pH of the aqueous phase controls the amount of carbonyl-substituted amino acid in the aqueous phase. The lower the pH, the more is contained in the aqueous portion. This allows for control of the enzymatic reaction rate. Because of the lower concentration of the L-amino acid derivative, i.e., carbonyl-substituted amino acid, in the aqueous phase, the formation of phenylalanine peptide is controlled.

The control of the equilibrium rate on partition from the organic phase into the aqueous phase as well as the pH control is also maintained in like manner when the hydrolysis is conducted external to the vessel containing the aqueous phase and the organic phase.

The process can be conducted statically or under agitation. Agitation can be strong enough to form finely dispersed droplets of one phase in the other. The two phase system should not be agitated sufficiently to form a stable emulsion as the two phases must be separated to isolate the product. The concentration of the desired amino acid can be above or below the limits of solubility under the reaction conditions. If the amino acid does precipitate, it can be easily filtered off. Agitation formed by pumping fractions in and out of the reactor is acceptable.

The process of the invention can be operated as a batch process or continuously, as desired. In a continuous process, precipitated L-amino acid can be continuously removed such as by filtration of the aqueous phase. Portions of the organic phase can be removed, racemized and returned to provide more L-isomer or, if the racemate is present as a water-soluble salt such as the hydrochloride, an organic solution can be prepared by dissolving the racemate in water, contacting with organic solvent, neutralizing the hydrochloride salt and separating off the aqueous phase. If a racemizing agent is used that can retard the effectiveness of the enzyme, good manufacturing practices may dictate removal of the agent before resolution.

The non-hydrolyzed isomer of the carbonyl-substituted amino acid can also be recovered from the organic solvent by any known separation technique, such as distillation, precipitation, or extraction as a hydrochloride salt. These HCl salts can be isolated and sold as such or the hydrolyzable group hydrolyzed.

After hydrolysis has proceeded to the desired point, the aqueous solution can be concentrated and neutralized whereby the D-isomer amino acid precipitates.

After substantially all of the L-isomer is separated from the organic phase, the concentrated D-isomer can be racemized by any known method such as high temperature. The enzymatic hydrolysis of the racemate can then be continued in the normal fashion.

In order to make the two phase solvent system resolution process economical, it is necessary that the non-hydrolyzed isomer, which remains substantially in the water-immiscible organic solvent after resolution, be racemized to allow further production of the amino acid of the other isomer. Any process for racemizing one isomer of a carbonyl-substituted amino acid in a water-immiscible solvent system must be under such conditions that the substituent group is not destroyed. Destruction of the substituent group would prevent further resolution in the protease enzyme hydrolysis procedure.

This beneficial result can be obtained by heating the solution of the carbonyl-substituted amino acid with an effective amount of an aliphatic acid in combination with an effective amount of an aldehyde or ketone at a temperature sufficient to effect racemization and preferably at reflux temperature for a period of time sufficient that at least 10% of the largest optical isomer is racemized. This is more fully disclosed in copending application of M. Empie, Ser. No. 642,212, filed Aug. 17, 1984, entitled "Method for Racemizing Derivatives of Alpha Amino Acids in Organic Media".

The optical isomer of the carbonyl-substituted alpha amino acid that is racemized can be either the L form, the D form or mixtures thereof. Any mixture less than the theoretical ratio of 50:50 can be racemized. Any degree of racemization, even partial racemization can be obtained in accordance with the present invention. By partial racemization is meant that at least 10% of the largest quantity of optical isomer has been converted to the corresponding D or L isomer. Preferably, at least 50% of the largest amount of optical isomer is racemized. By racemized is meant the conversion of the optically active form to an optically inactive form, consisting of equal mixtures of D and L forms.

The optically active isomers of hydrolyzable amino acid derivatives with underivatized alpha amino nitrogen that can be racemized can be represented by the formula:

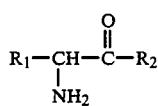

(VIII)

wherein $R_1$ and $R_2$ are as defined hereinbefore.

Examples of the represented parent amino acids, i.e. as if $R_2$ were hydroxyl, include valine, leucine, isoleucine, serine, threonine, methionine, phenylalanine, tyrosine, tryptophan, 3,4-dihydroxyphenylalanine, 2,4-dihydroxyphenylalanine, 3,4-methylenedioxyphenylalanine, 3,4-dimethoxyphenylalanine, 3,4-isopropylidenedioxyphenylalanine, 3,4-cyclohexylidenedioxyphenylalanine, 5-hydroxytryptophan, 5-methyltryptophan and 3,4,5-trihydroxyphenylalanine.

The amino acids used in the invention are generally in the form of hydrolyzable derivatives. The moiety attached to the carbonyl group of the amino acid is preferably hydrolyzable such as by an enzyme in order to form the desired isomer of the free amino acid.

The D- and L-isomeric derivatives must be soluble in water and organic solvent, and one of the isomers must be hydrolyzable by an isomer selective enzyme at the carbonyl group to produce the corresponding amino acid. Preferably, the hydrolyzable group is the ester and preferably the ester is methyl or ethyl.

Preferably the amino acid is phenylalanine or ring-substituted derivatives thereof including hydroxy, halo, alkyl and nitro groups. The preferred hydrolyzable group is the ester. Preferably the ester is the methyl or ethyl ester. The remaining description of the invention will be discussed in connection with the preferred amino acid, phenylalanine, and its esters though the teachings will apply equally to other named amino acids and hydrolyzable derivatives.

The racemization reaction is conducted in a substantially anhydrous organic medium of a substantially water-immiscible organic material as defined above which is a solvent for the racemate but is not a solvent for the corresponding amino acid under the conditions of the reaction. By "substantially anhydrous" it is intended to mean that the organic solvent medium contains less than 5% moisture on a weight basis. The organic material can be any immiscible or partially miscible organic solvent which is not reactive with the ester as can be illustrated by toluene, methylene chloride, cyclohexanone, ethyl acetate, butyl acetate, butanol and the like, and mixtures thereof with toluene being preferred. The carbonyl-substituted amino acid can also act as the solvent itself. The carbonyl-substituted amino acid, e.g. a phenylalanine ester, content of the organic solvent can range from about 100% to about 2% with from about 30% to about 2% on a weight per volume basis being preferred.

The solution to be racemized can be prepared separately or it can occur as the result of a resolution process. An organic solvent system can be used to dissolve the carbonyl-substituted amino acid or the carbonyl-substituted amino acid as its hydrochloride can be extracted into the organic solvent, e.g. toluene, by neutralization. The solution to be racemized can also be the result of a resolution reaction utilizing an oranic solvent phase containing unhydrolyzed isomer.

In a preferred embodiment of the present invention, the solution to be racemized is the result of an enzyme hydrolysis process for resolving amino acids, e.g. D,L-phenylalanine, by the use of an organic solvent-aqueous system wherein a majority of the carbonyl-substituted amino acid concentrates in the solvent phase.

As the racemization reaction is more conducive at elevated temperatures, it is preferred that the apparatus be adapted to allow for sufficient heating of the organic solvent system. Glass apparatus can also be adapted to accommodate pressures up to 5 psig (0.3 atmospheres) as a means of increasing the temperature of reaction above that of reflux. Still higher temperatures can be attained in metal equipment resistant to still higher pressures.

The aliphatic acids usable in the invention can be depicted by the formula:

wherein $R_5$ is hydrogen or an aliphatic carbon chain of from $C_1$ to about $C_6$ and preferably from $C_1$ to about $C_3$. Suitable examples of aliphatic carboxylic acids usable in the invention include formic, acetic, propionic, butyric and valeric acids.

Suitable aldehydes and ketones for use in the invention can be depicted by the formula:

$$R_6C(O)R_7$$

wherein $R_6$ and $R_7$ can be hydrogen; from about $C_1$ to about $C_8$ alkyl; from $C_1$ to about $C_8$ alkenyl; phenyl, substituted phenyl having a substituent selected from the group of hydroxy, nitro, halo (F, Cl, Br and I), sulfoxy, amino and alkoxy (from $C_1$ to about $C_5$), phenylvinyl, hydroxynaphthyl and nitrogen-containing heteromonocyclic. $R_6$ is preferably from $C_1$ to about $C_8$ alkyl, and phenyl. Representative examples of aldehydes and ketones included within this group can be illustrated by: acetaldehyde, propionaldehyde, n-butyraldehyde, isobutyraldehyde, n-valeraldehyde, caproaldehyde, n-heptylaldehyde, acrylaldehyde (i.e. acrolein), methacrylaldehyde (i.e. methacrolein), salicylaldehyde, benzaldehyde, polyvinyl methyl ketone, m-hydroxybenzaldehyde, p-hydroxybenzaldehyde, o-nitrobenzaldehyde, m-nitrobenzaldehyde, nitrosalicylaldehyde, anisaldehyde, vanillin, alpha-naphthylaldehyde, dihydroxybenzaldehyde, p-methyl, m-hydroxybenzaldehyde, 2-thienylcarboxaldehyde, 2-pyridinylcarboxaldehyde, nicotinic aldehyde and the like, phenylacrolein, furfural and nitrofurfural, cyclohexanone, methylethyl-ketone. Cyclohexanone as sole solvent can form non-reactive adducts but can be used in limited amounts with acetic acid as catalyst.

The aliphatic acid is preferably used in an amount ranging from about 5 to about 150 mole percent of the amino acid ester. The aldehydes are preferably used in an amount ranging from about 0.6 to about 21 mole percent based on the amino acid ester. The aliphatic acid is used in a ratio to the aldehyde in an amount ranging from about 250:1 to about 1:1. The organic solvent amino acid derivative solution has less than 20 weight percent aliphatic acid and less than 10 weight percent aldehyde or ketone and preferably from about 0.3 to about 5 weight percent aliphatic acid and from about 0.3 to about 1 weight percent aldehyde or ketone. The derivative such as the ester in the organic solvent concentration can be from about 1% to about 30% and preferably from about 3% to about 15%.

The racemization reaction is preferably carried out by blending an optically active alpha amino acid derivative such as the ester with an inert solvent, the aliphatic acid and the aldehyde. Agitation is preferably applied to insure even blending and uniform heat transfer.

It is desirable to tie up the free amino group to prevent peptidization during racemization. A convenient method for accomplishing this result is bubbling hydrogen halide gas such as hydrogen chloride gas through the liquid before racemization. Other convenient methods include treating the amino acid with mineral acids such as $H_2SO_4$.

The temperature conditions within the organic system are such as to be conducive to the racemization reaction. The temperature of reaction can range from about 50° to about 120° C. and preferably from about 90° C. to about 115° C. and most preferably at reflux. The reaction is preferably conducted at atmospheric pressure though pressures of up to 15 atmospheres can be used. The pH of the reaction system can range from about 1 to about 8, preferably from 1 to about 5. The racemization reaction is conducted for a period of time sufficient to racemize at least 10% of the optical ester of the larger quantity and preferably for a period of time sufficient to racemize at least 50%. The time for racemization generally ranges from about 1 to about 5 hours, though less or more time may be used depending on conditions.

The process of the invention can be operated as a batch process or as a continuous process, especially in combination with an optical isomer resolution process as part of the overall process. Portions of the organic phase can be withdrawn from the system either totally or in part depending on whether a batch process or a continuous process is being undertaken. It is not necessary that the resolution be undertaken on a pure optical isomer since blends of the D and L-isomers wherein one is substantially larger than the other can be racemized by the present invention to the limit of 50:50 D to L isomer.

It is desirable that the organic solvent, e.g. toluene, be essentially anhydrous to avoid hydrolyzing the carbonyl-substituted amino acid ester. This can be accomplished by drying the toluene solution using any known method such as by drying over a drying agent such as magnesium sulfate (anhydrous).

The racemate can be recovered in a form for further resolution. Also, the D,L-racemate can be directly recovered by conventional means such as distillation and crystallation. The racemate can be recovered as the water soluble mineral acid salt or the salt can be neutralized to obtain the solvent-soluble compound.

The optical isomer of the carbonyl-substituted alpha amino acid in a substantially anhydrous organic solvent can also be racemized without destruction of the substituent group by heating the solution with an effective amount of pyridoxal phosphate a temperature sufficient to effect racemization and preferably at reflux temperature for a period of time sufficient that at least 10% of the largest optical isomer is racemized. This is disclosed in copending application of M. Empie, Ser. No. 641,889, filed Aug. 17, 1984, entitled "Method for Racemizing Derivatives of Alpha Amino Acids in Organic Media". Preferably, the pyridoxal-5-phosphate is immobilized such as on an ion exchange resin. By this method, a solution of optical isomer in organic solvent substantially free of water can be racemized without destruction of the carbonyl substituent group functionality.

The racemization reaction is conducted in a substantially anhydrous organic medium of a substantially water-immiscible organic material as defined hereinbefore.

The solution to be racemized can be prepared separately as defined hereinbefore or it can occur as the result of a resolution process. An organic solvent system can be used to dissolve the amino acid or the carbonyl-substituted amino acid as its hydrochloride can be extracted into the organic solvent, e.g. toluene, by neutralization. The solution to be racemized can also be the result of a resolution reaction utilizing an organic solvent phase containing unhydrolyzed isomer.

In a preferred embodiment of the present invention, the solution to be racemized is the result of an enzyme hydrolysis process for resolving amino acids, e.g. D,L-phenylalanine, by the use of an organic-aqueous solvent, or two phase system wherein a majority of the carbonyl-substituted amino acid concentrates in the solvent phase while the hydrolysis occurs in the aqueous phase.

As the racemization reaction is more conducive at elevated temperatures, it is preferred that the apparatus be adapted to allow for sufficient heating of the organic solvent system. Apparatus can also be adapted to accommodate pressure up to 5 atmospheres as a means of increasing the temperature of reaction above that of reflux.

To effect racemization of the optical isomer the pyridoxal-5-phosphate can be added directly to the organic phase though this is less preferred since the catalyst is expensive and is desirably used in a recoverable form. Preferably, the pyridoxal-5-phosphate is immobilized on a matrix such as an anion exchange resin which will bind the negatively charged phosphate. Illustrative of an ion exchange resin is the type sold under the trademark WHATMAN DE52, a brand of cellulosic anion exchange resin. Other resins which could be used are well within the knowledge of a skilled artisan.

The immobilized catalyst is prepared using standard techniques which include washing the ion exchange resin with dilute acid followed by soaking the ion exchange resin in a neutral pH (6.5-7.5) solution of the pyridoxal-5-phosphate to attach the same thereto.

The immobilized catalyst can be placed directly into the vessel containing the organic solvent and the carbonyl-substituted amino acid or the organic solvent system can be pumped through a vessel containing the immobilized catalyst. As the racemization reaction is a high temperature reaction, it is preferred that the apparatus be adapted to allow heating at the same time that the catalyst is in contact with the organic solvent system. Agitation may be required to allow even blending and uniform heat transfer.

The amount of pyridoxal-5-phosphate used can range from about 0.1 to about 200 moles percent ester to pyridoxal-5-phosphate based on the ester to be racemized with a preferred molar percent of from about 1 to about 100.

The temperature conditions within the organic system are such as to be conducive to the racemization reaction. The temperature of reaction can range from about 50° C. to about 120° C. and preferably from about 90° C. to about 115° C. and most preferably at reflux. The reaction is preferably conducted at atmospheric pressure though pressures of up to 15 atmospheres can be used. The racemization reaction is conducted for a period of time sufficient to racemize at least 10% of the optical ester of the larger quantity and preferably for a period of time sufficient to racemize 50%. The time for racemization generally ranges from about 1 to about 5 hours, depending on conditions though less or more time may be used.

The process of the invention can be operated as a batch process or as a continuous process, preferably in combination with an optical isomer resolution process. Portions of the organic phase can be withdrawn from the system either totally or in part depending on whether a batch process or a continuous process is being undertaken. It is not necessary that the racemization be undertaken on a pure optical isomer since blends of the D and L-isomers wherein one is present in substantially larger concentrations than the other can be racemized by the present invention to the limit of 50:50 D to L isomer.

It is desirable that the organic solvent, e.g. toluene, be anhydrous to avoid hydrolyzing the carbonyl-substituted amino acid. This can be accomplished by drying the toluene blend using any known method such as by drying over a drying agent such as magnesium sulfate (anhydrous).

The racemate can be recovered in a form for recycling for further resolution. Also, the D,L-racemate can be directly recovered by conventional means such as distillation or crystallization. The racemate can be recovered as the water soluble mineral acid salt or the salt is neutralized to obtain the solvent soluble compound.

The L or single isomer amino acid product of the process of the invention finds many known uses, particularly L-phenylalanine which is a precursor for the preparation of aspartame, an artifical sweetner.

The invention will be illustrated in the examples which follow:

EXAMPLE 1

This example illustrates the preparation of 5-benzalhydantoin from hydantoin and benzaldehyde.

A mixture of 25 g. hydantoin (0.25 mole), 29.3 g. benzaldehyde (0.275 mole) and 125 ml water as solvent were placed in a round bottom flask fitted with stirrer, condenser, thermometer, and heating mantle. Then, 9.9 g. of ammonium bicarbonate (0.125 mole-50 mole % based on hydantoin) was added with stirrring over a period of 10 minutes. A considerable amount of white solid formed. The mixture was stirred at reflux for 4 hours. Solids crystallized out on cooling to room temperture. The solid was suction filtered, water washed and then ethanol washed. 45 g. of a white solid determined by UV analysis to be 5-benzalhydantoin was obtained. The theoretical yield based on starting material was 96%. The 5-benzalhydantoin had a melting point of 215°-221° C. which corresponds to the melting point of 218°-220° C. reported in BIOCHEM J. 29, 542 (1935).

The following examples illustrate the preparation of 5-benzylhydantoin from benzalhydantoin using a Raney Nickel catalyst and sodium hydroxide.

EXAMPLE 2

A 250 ml round bottom flask, fitted with a stirrer, dip tube, thermometer, and condenser was charged with 5 g. of benzalhydantoin, 75 ml methanol and 75 ml water, 1.2 g. of NaOH (100 mole % based on benzalhydantoin) and 1 g. of No. 2800 Raney Nickel (Davison Div.—W. R. Grace). Hydrogen was bubbled in with vigorous stirring. The temperature was held at approximately 40° C. After 7 hours of stirring, the hydrogenation as measured by UV analysis was 42% complete; after 14 hours, 64% complete and at 23 hours, 95% complete. Liquid chromatography showed the reaction to be 96-98% complete. The product consisted of 21% 5-benzylhydantoin, 71% N-carbamylphenylalanine, 2% phenylalanine and 4% unreacted benzalhydantoin. All were present as sodium salts.

EXAMPLE 3

Example 2 was repeated using 5 grams of 5-benzalhydantoin, 150 milliliters of distilled water as diluent, 1.4 grams of NaOH (113 mole % based on benzalhydantoin) and 1.0 gram of No. 2800 Raney Nickel. After 8 hours of hydrogen addition with stirring, there was observed over 95% complete hydrogenation by UV analysis and 100% completion as measured by liquid chromatography analysis. The product consisted mainly of the sodium salt of N-carbamylphenylalanine with a small amount of 5-benzylhydantoin present.

EXAMPLE 4

A 500 milliliter round bottom flask fitted as above was charged with 300 milliliters of deoxygenated distilled water, 30 grams of benzalhydantoin, 9.5 grams of NaOH (150 mole % based on benzalhydantoin) and then 1.5 grams of No. 2800 Raney Nickel (5 wt. % based on benzalhydantoin) were added. After 5 hours of stirring and $H_2$ flow, the reduction was 53% complete; at 12.75 hours, 92% complete by UV analysis; at 19 hours, the reaction was 100% complete by liquid chromatography and UV analysis. The product was essentially all N-carbamylphenylalanine with a trace of 5-benzylhydantoin.

EXAMPLE 5

Similar to Example 3 above except 1.8 grams (172 mole %) of NaOH was used. The reaction was done in 7 hours (over 98% complete based on UV analysis). Liquid chromatographic analysis showed the product to consist of 47.8% 5-benzylhydantoin, 50.2% N-carbamylphenylalanine, 0.3% phenylalanine and 1.7% 5-benzalhydantoin. The catalyst was then filtered off. The filtrate was neutralized with hydrochloric acid to pH 7–8. Upon evaporation to dryness, the filtrate gave 8 g. of white solid. The amount of NaCl present was determined by titration and the yield of benzylhydantoin/N-carbamylphenylalanine was essentially quantitative. After thorough washing with water to remove salt, the remaining solid had a melting point of 188° C.–190° C.

EXAMPLE 6

A 500 milliliter Parr pressure bottle was charged with 30 grams of benzalhydantoin, 300 milliliters of distilled water, 12.7 grams of NaOH and 1.5 grams No. 2800 Raney Nickel. The bottle was pressurized with hydrogen to 50 psig and shaken on a Parr apparatus. The pressure was maintained at 30–50 psig with an average of 40 psig. After 8 hours of hydrogenation at 25° C. the reaction was 92% complete based on UV analysis and 100% complete after 10 hours. Liquid chromatographic analysis showed 0.8% phenylalanine, 92.0% N-carbamylphenylalanine, 2.3% 5-benzylhydantoin, 1.3% phenylpyruvic acid and 1.6% benzalhydantoin, all present as the sodium salts.

EXAMPLE 7

Same as Example 6 except a 500 ml round bottom flask was used and the $H_2$ was added at atmospheric pressure and 50°–55° C. After 7 hours, the reaction was 76% complete; at 14.5 hours, over 95% complete based on UV analysis.

EXAMPLE 8

Similar to Example 7 except for the higher temperature of 50°–80° C. The reaction was 100% complete in 15–16 hours based on UV analysis. The product contained 9% phenylpyruvic acid and 4% phenylacetic acid as the sodium salts.

These Examples illustrate the reduction of 5-benzalhydantoin to benzylhydantoin or its ring opened derivative, N-carbamylphenylalanine using zinc and hydrochloric acid.

EXAMPLE 9

This Example shows the process in which hydrochloric acid is added first and then the zinc is added. A round bottom flask fitted with a stirrer, thermometer and condenser was charged with 10 grams of 5-benzalhydantoin (0.053 mole), 100 milliliters of methanol and then 21.0 grams of concentrated (37 weight percent) hydrochloric acid (0.213 mole of hydrogen chloride, 400 mole percent based on 5-benzalhydantoin) was added. To this was added very slowly with stirring 6.93 grams of zinc powder (0.106 mole, 200 mole percent based on 5-benzalhydantoin) over a period of 45 minutes. After 30 minutes of additional stirring, some of the zinc powder remained unreacted and so 5 grams more of concentrated hydrochloric acid was added. After about 60 minutes more of stirring, no unreacted zinc powder remained. The reaction was stirred an additional 2 hours. By UV analysis, the reaction mixture showed 98% reduction of the carbon-carbon double bond of the 5-benzalhydantoin. By workup of the reaction mixture N-carbamylphenylalanine was isolated. The melting point was determined to be 186°–188° C. corresponding to the literature melting point of 190° C., reported in Am. Chem. J. 45, 368 (1911) (compound referred to as 4-benzylhydantoic acid).

EXAMPLE 10

This Example shows the effect of adding the hydrochloric acid to zinc. Similar to Example 9 above, the flask was charged with 10.0 grams of 5-benzalhydantoin and 100 milliliters of methanol. Seven grams of zinc powder (0.106 mole) was then added. Twenty-one grams of concentrated (37 weight percent) hydrochloric acid (0.213 mole of hydrogen chloride, 400 mole percent based on 5-benzalhydantoin) was added with stirring over a 30 minute period. The temperature rose to 52° C. All of the insoluble benzalhydantoin was dissolved after about 75% of the hydrochloric acid was added. The reaction mixture was stirred for 1 hour at 50° to 55° C. but some zinc was still unreacted. Therefore, 5 grams more of hydrochloric acid was added and after 30 minutes more of stirring, essentially all of the zinc had reacted. UV analysis showed that over 95% of the 5-benzalhydantoin had reacted yielding the saturated hydantoin and/or ring opened saturated N-carbamylphenylalanine.

These Examples illustrate the hydrolysis of benzylhydantoin to phenylalanine using sodium hydroxide.

EXAMPLE 11

Three grams (0.016 mole) benzylhydantoin was mixed with 6 grams of 30% sodium hydroxide (2.8 molar equivalents) and 1.5 milliliters water in a round bottom flask equipped with a magnetic stirrer and reflux condenser. After the mixture was heated at reflux for 6 hours, 81% of the benzylhydantoin had been converted to phenylalanine as determined by high pressure liquid chromatography. After 14 hours heating, 84% hydrolysis had been achieved.

EXAMPLE 12

This Example shows that the rate of hydrolysis is increased when greater than 5 molar equivalents of an alkali metal hydroxide are used.

The procedure of Example 11 was repeated using 12 milliliters of 30% sodium hydroxide (5.6 molar equivalents) and 3 milliliters water. After 6 hours at reflux, the extent of hydrolysis was 73% and 100% after 14 hours. Using 4 molar equivalents, the hydrolysis reaction proceeded to completion whereas in Example 11 using 2.8 molar equivalents hydrolysis appeared to have ceased at 84% yield after the same time.

EXAMPLE 13

The procedure of Example 11 was repeated using 12 grams of 20% sodium hydroxide (3.75 molar equivalents) and no extra water. Hydrolysis yield of 96% was achieved after 7 hours of heating at reflux.

EXAMPLE 14

The procedure of Example 11 was repeated using 5 grams of 50% sodium hydroxide (3.9 molar equivalents) and 4.5 grams water. After 11 hours, the extent of hydrolysis was 92%.

These Examples illustrate the hydrolysis of benzylhydantoin to phenylalanine using acid conditions.

EXAMPLE 15

0.1 grams (0.00052 mole) of benzylhydantoin was admixed with 0.16 grams $H_2SO_4$ (98% concentrated) and 0.24 gram water. This was placed in a glass tube sealed at the bottom. The top was sealed by melting the glass using a torch. The sealed tube was placed in a lead pipe for explosion protection and then in a silicone oil bath and heated to 150° C. The tube was maintained in the bath for 5.5 hours. After removing and cooling, the tube was broken open. Analysis of the contents by high pressure liquid chromatography showed 92% hydrolysis (two peaks of starting materials and final product) as compared to standards.

EXAMPLES 16, 17 AND 18

Example 15 was repeated using the materials and conditions listed below. Yields of 84% to 97% were obtained.

TABLE I

| Ex. | Benzyl-Hydantoin | $H_2SO_4$ | $H_2O$ | Temp. | Time Hours | Yield % |
|---|---|---|---|---|---|---|
| 16 | 0.1 g (.00052 M) | .08 g (.00082 M) | 32 g (.0178 M) | 60° C. | 24 | 84 |
| 17 | 0.2 g | 0.16 g* | 0.24 g | 150° C. | 5.5 | 97 |
| 18 | 0.1 g | 0.16 g* | 0.24 g | 110° C. | 4 | 93 |

*0.4 gram 40% $H_2SO_4$ = 0.16 gram $H_2SO_4$ and 0.24 gram $H_2O$

The following Examples illustrate the resolution of an ester of D,L-phenylalanine to L-phenylalanine. D,L-phenylalanine esters can be prepared by (a) forming a 20% solution of phenylalanine in methanol and saturating the solution with HCl gas (whereupon the phenylalanine dissolves—a noticeable temperature rise to 50°–70° C. occurs); (b) cease HCl addition and (c) reflux the solution for 4–8 hours. The methanol is stripped thereby removing the excess HCl and a dry solid phenylalanine methyl ester hydrochloride is obtained. The hydrochloride can be dissolved in water preparatory to resolution.

EXAMPLE 19

A mixture of 1.15 grams of D,L-phenylalanine methyl ester in 2.5 milliliters of water was added to 5.0 milliliters of ethyl acetate. The pH was adjusted to 6.5 with 2.5 milliliters of sodium hydroxide. Two milligrams of chymotrypsin was added and the reaction was stirred gently at room temperature. A white precipitate appeared after 1.5 hours. The precipitate was isolated after 2 hours yielding 0.22 grams with an optical rotation equivalent to 98% pure L-phenylalanine.

EXAMPLE 20

A 0.2 molar solution phenylalanine methyl ester in 10 milliliters of water was prepared. Toluene was added and the pH of the system adjusted to 7.0 with sodium hydroxide. Chymotrypsin in the amount of 1 milligram was added. The concentration of phenylalanine in the aqueous phase was monitored. The initial concentration was 0.05 molar and the final concentration at the end of the hydrolysis was 0.15 molar, consistent with only one isomer being extracted.

EXAMPLE 21

A solution of 2.29 grams of D,L-phenylalanine methyl ester hydrochloride in 10 milliliters of water was prepared. Ten milliliters of toluene was added and the pH of the aqueous phase of the biphase mixture was adjusted to 6.8 with sodium hydroxide. The mixture was allowed to separate and the aqueous phase (or lower phase) was connected to a pump via tubing. The pump was then connected to a filter. A portion of the aqueous phase was pumped through the filter into a column containing chymotrypsin enzyme immobilized in Sepharose ™ 4B (Pharmacia). The effluent from the column was then pumped back into the biphase reaction mixture. The initial pH of the enzyme column effluent was 6.2. After 5 hours the pH increased to 6.8. The pH in the biphase reaction mixture was constant at 6.8. L-phenylalanine precipitated in the aqueous phase and was recovered by the filter with an overall yield of 85% based on the theoretical amount of recoverable phenylalanine after correcting for water saturation.

EXAMPLE 22

To 50 milliliters of a 3% weight per volume presaturated solution of L-phenylalanine was added 10.0 grams D,L-phenylalanine ethyl ester hydrochloride and 50 milliliters of toluene. The biphase mixture was neutralized to a pH of 6.8 with 50% sodium hydroxide and 25 milligrams chymotrypsin enzyme was added. The reaction proceeded for 3.5 hours whereupon the precipitate which formed during the reaction was filtered out and washed with small amounts of water. A total of 1.9 grams of L-phenylalanine was obtained with 98% purity by optical rotation.

The toluene from the reaction was separated from the aqueous layer and the D-phenylalanine ester contained therein was racemized. The toluene and racemized ester were returned to the aqueous phase where a second hydrolysis reaction was undertaken to further resolve the racemized D,L-phenylalanine ester. A second precipitate was obtained in an amount of 1.5 grams which was 96% L-phenylalanine.

EXAMPLE 23

D,L-phenylalanine methyl ester hydrochloride was extracted into toluene by neutralization with sodium hydroxide to give a 9.2% solids solution. An aliquot of 300 milliliters was placed in contact with 210 milliliters of water. The pH of the mixture was adjusted to 6.8. The temperature was raised to 40° C., chymotrypsin immobilized as in Example 21 was added and the reaction mixture was stirred for 6 hours until the reaction was complete. The enzyme was filtered out and the aqueous portion separated. The aqueous portion was cooled overnight at 4° C. 4.6 grams of precipitated L-phenylalanine of 92% purity by optical rotation was obtained. This represents 84% yield after correcting for water saturation.

The following Examples illustrate the racemization of an optical isomer of phenylalanine ester using glacial acetic acid and benzaldehyde.

EXAMPLE 24

To a solution of 2 grams L-phenylalanine ethyl ester dissolved in 30 milliliters of toluene was added 1 milliliter glacial acetic acid and 0.1 milliliters benzaldehyde. The solution was refluxed for 4 hours. The ester was completely recovered and optical rotation measurements showed complete racemization.

EXAMPLE 25

A mixture of 1 gram of D-phenylalanine methyl ester in 10 milliliters of toluene resulting from an enzymatic resolution of a racemic mixture of the esters was treated by bubbling dry HCl gas through the solution until an aliquot of the toluene yielded a pH below 4 when added to water. 0.2 milliliters of glacial acetic acid and 0.1 milliliter of benzaldehyde was then added to the solvent mixture and the mixture was refluxed for 3 hours. The solvent was then stripped and the 1.12 grams of recovered solid was dissolved in 10 milliliters of water. The pH of the latter solution was adjusted to 6.2 and placed on a pH stat (Brinkman). Chymotrypsin enzyme was then added. The acid released was titrated to yield 93% of a theoretical racemic mixture.

EXAMPLE 26

D,L-phenylalanine ethyl ester in an amount of 76.5 grams was enzymatically resolved to L-phenylalanine using chymotrypsin in a two-phase toluene-water system. At the end of the resolution, substantially all of the D-phenylalanine ethyl ester was contained in the toluene (300 milliliters). The toluene was separated and dried over $MgSO_4$.

The dry toluene was acidified by bubbling dry HCl through it until a pH of an aliquot mixed with water was about 2.3. One milliliter of glacial acetic acid and 0.1 milliliter benzaldehyde was added and the mixture refluxed for 3 hours. The toluene-ester mixture was cooled, neutralized and added back to the aqueous portion of the enzyme reaction system. A second resolution was allowed to proceed resulting in the recovery of additional L-phenylalanine.

The following Examples illustrate the racemization of an optical isomer of phenylalanine ester using pyridoxal-5-phosphate.

EXAMPLE 27

Pyridoxal-5-phospate ion exchange resin was prepared by adding 500 milligrams of the compound to 3 grams of an ion exchange resin (WHATMAN brand DE52). After standing, the resin was filtered and washed two times with water followed by dehydrating with ethyl alcohol. L-phenylalanine ethyl ester hydrochloride in an amount of 3 grams was dissolved in water and extracted into toluene by neutralization. The toluene was removed and dried over $MgSO_4$ (anhydrous). The pyridoxal-5-phosphate ion exchange resin was added to the dehydrated toluene containing the L-phenylalanine ethyl ester. The mixture was refluxed at a temperature of about 110° C. for about 1.5 hours. Forty-nine and one-half percent of the original L-phenylalanine ester was converted to the D isomer as determined by optical rotation measurements.

EXAMPLE 28

10.0 grams D,L-phenylalanine ethyl ester hydrochloride was dissolved in a two-phase enzyme resolution system consisting of equal 50 milliliter volumes of toluene and water saturated with L-phenylalanine. The water phase also contained chymotrypsin enzyme. The resolution reaction was allowed to proceed to completion whereupon the toluene containing the D-phenylalanine ethyl ester was removed, dried with $MgSO_4$ and added to 3 grams of pyridoxal resin prepared as in Example 27. The toluene-ester-resin solution was refluxed for 6 hours. Optical rotation measurements indicate 85% conversion to a racemic mixture. The resin was filtered from the toluene and the toluene returned to the enzyme resolution system. A second enzymatic resolution took place, resulting in a second crop of L-phenylalanine.

Additional features of the preferred and most preferred embodiments of the present invention are found in the claims.

What is claimed:

1. A process for preparing racemates of alpha amino acids comprising:
   (a) producing an unsaturated hydantoin by condensing a hydantoin with an aldehyde in the presence of at least one basic salt of an inorganic acid, said unsaturated hydantoin having the formula:

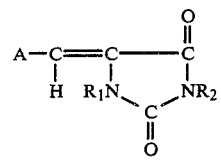

wherein A is X or Y and X is unbranched or branched alkyl or alkenyl, cycloalkyl, cycloalkenyl, alkylthio, hydroxyalkyl, aralkyl, mono or dialkylaminoalkyl, acylaminoalkyl, mercaptoalkyl, cycloalkyl having a —$CH_2$— group replaced by —O—, —S—, or —NH—, cycloalkenyl having a —CH= replaced by —O—, —S—, or —N—; Y is

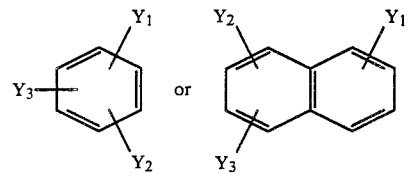

wherein $Y_1$, $Y_2$, and $Y_3$ are the same or different and are hydrogen, alkyl, alkenyl, cycloalkyl, cycloalkenyl, aryl, halogen, hydroxy, nitro, cyano, amino, alkylaminoalkyl, dialkylaminoalkyl, alkoxy, alkylthio, acyloxy, mercaptoalkyl, alkaryl, aralkyl, acylaminoalkyl, cycloalkyl having a —$CH_2$— group replaced by —O—, —S—, or —NHR—, cycloalkenyl having a —CH= replaced by —N— or where two of the members, $Y_1$, $Y_2$, and $Y_3$, are joined together to form an alkylene group having at least one —$CH_2$— group replaced by —O—, —S—, or —NH= or an alkenylene group having at least one —CH= group replaced by —N=; and $R_1$ and $R_2$ are the same or different and are hydrogen, alkyl, aryl, acyl, or amino;

(b) reducing said unsaturated hydantoin with hydrogen using a nickel catalyst in the presence of more than a stoichiometric amount of caustic or using zinc in the presence of hydrochloric acid to produce saturated hydantoins and/or ring opened derivatives thereof; and (c) hydrolyzing the product of step (b) by heating to a temperature sufficient to hydrolyze the product of step (b) with at least 3 molar equivalents of an alkali metal hydroxide or a mineral acid under from 1 to 5 atmospheres pressure to produce racemates of alpha amino acids.

2. The process of claim 1 wherein the amount of caustic is from 100 to 250 mole percent based on the amount of unsaturated hydantoin.

3. The process of claim 2 wherein the amount of caustic is from about 110 to about 180 mole percent based of the amount of unsaturated hydantoin.

4. The process of claim 1 wherein the amount of nickel catalyst is from about 1% to about 50% based on weight of the unsaturated hydantoin.

5. The process of claim 4 wherein the amount of nickel catalyst is from about 2% to about 30% based on weight of the unsaturated hydantoin.

6. The process of claim 1 wherein the temperature of the nickel catalyzed reduction ranges from about 10° to about 65° C.

7. The process of claim 1 wherein the molar equivalents of alkali metal hydroxide in step (c) range from about 3 to about 7.

8. The process of claim 1 wherein the amount of zinc ranges from about 100 to about 400 mole percent based on the amount of unsaturated hydantoin and the amount of hydrochloric acid is from about 200 to about 400 mole percent based on the amount of zinc added.

9. The process of claim 1 wherein there is employed at least 0.1 mole of the basic salt of the inorganic acid per mole of reacting hydantoin.

10. The process of claim 1 wherein the temperature is 10° to 105° C.

11. The process of claim 1 wherein the basic salt is a salt of an inorganic acid having a $pK_a$ above 5.

12. The process of claim 1 wherein the inorganic acid is carbonic acid, the bicarbonate of carbonic acid, or the monoacid phosphate of phosphoric acid.

13. The process of claim 1 wherein the basic salt is ammonium carbonate or bicarbonate.

14. The process of claim 1 wherein said hydantoin or ring opened derivative or alkali metal salts thereof is heated with from about 5 to about 7 molar equivalents of an alkali metal hydroxide, assuming the hydantoin or derivative are at neutral pH at a temperature ranging from about 70° C. to about 100° C. for a period of time sufficient to effect at least 70% hydrolysis.

15. The process as recited in claim 14 wherein said period of time ranges from about 4 to about 25 hours.

16. The process of claim 1 which includes the further step of reacting the amino acid with a reactant effective to form a resolvable derivatized amino acid racemate.

17. The process of claim 1 which includes the further step of reacting the amino acid with a reactant effective to form an alpha amino acid racemate derivative, said alpha amino acid substituted at the carbonyl group wherein the substituent can be selectively removed to resolve the racemate and wherein the alpha amino nitrogen is unsubstituted.

18. The process of claim 1 which includes the further step of esterifying said amino acid.

19. The process of claim 18 wherein said ester product is methyl or ethyl.

20. The process of claim 16 which includes the further step of resolving the resolvable amino acid racemate.

21. The process of claim 17 which includes the further step of resolving the resolvable amino acid racemate.

22. The process of claim 21 wherein said racemate of optically active amino acids substituted at the carbonyl group wherein the alpha amino acid nitrogen is underivatized is resolved by a process comprising:

(a) preparing a two-phase system of a racemate of an amino acid substituted at the carbonyl group, wherein the alpha amino nitrogen is underivatized, dissolved in a substantially anhydrous water-immiscible organic material which is a solvent for said amino acid racemate, but not for the corresponding amino acids to form an organic phase and in water to form an aqueous phase wherein the racemate dissolved in the aqueous phase is in equilibrium with the racemate in the organic phase;

(b) selectively hydrolyzing with an enzyme one of the optical isomers of the amino acid racemate in the aqueous phase to the corresponding amino acid; and (c) recovering the amino acid.

23. The process as recited in claim 19 wherein the amino acid substituted at the carbonyl group is a $C_1$-$C_8$ ester of said amino acid.

24. The process according to claim 23 wherein the ester is methyl or ethyl.

25. The process according to claim 22 wherein the enzyme is chymotrypsin.

26. The process according to claim 22 wherein the organic material is selected from the group consisting of toluene, methylene chloride, cyclohexanone, butyl acetate, ethyl acetate, and mixtures thereof.

27. The process according to claim 22 wherein the hydrolysis is accomplished by passing the aqueous solution through an immobilized enzyme external to the contacted aqueous solution and organic material.

28. The process of claim 22 wherein the organic material to water volume ratio ranges from about 10:1 to about 1:10 and the racemate content of the organic material can range from about 100% to about 5%.

29. The process of claim 22 wherein the amino acid substituted at the carbonyl group is a phenylalanine substituted at the carbonyl group and the amino acid recovered after resolution is L-phenylalanine.

30. The process of claim 22 which includes the further step of racemizing the optical isomer not selectively resolved to the extent of at least 10% of the isomer.

31. The process of claim 30 wherein the unresolved optical isomer of the alpha amino acid substituted at the carbonyl group is in a substantially anhydrous water-immiscible inert organic solvent and is racemized by heating the solution of said optical isomer in said inert substantially anhydrous water-immiscible organic solvent in combination with an effective amount of an aliphatic acid and an effective amount of an aldehyde or ketone to a temperature within the range of from about 50° to about 120° for a period of time sufficient to racemize at least 10% of said isomer.

32. The process according to claim 31 wherein said optical isomer is a $C_1$–$C_8$ ester of an alpha amino acid.

33. The process according to claim 32 wherein the amino acid ester is an ester of phenylalanine.

34. The process according to claim 31 wherein the substantially anhydrous water-immiscible inert organic solvent is selected from the group consisting of toluene, methylene chloride, cyclohexanone, ethyl acetate, butyl acetate, butanol and mixtures thereof.

35. The process according to claim 31 wherein the aliphatic acid is acetic acid and the aldehyde is benzaldehyde.

36. The process according to claim 31 wherein the aliphatic acid is used in an amount ranging from about 15 to about 150 mole percent and the aldehyde or ketone in an amount ranging from about 0.6 to about 21 mole percent based on the amino acid derivative and the ratio of said aliphatic acid to said aldehyde ranges from about 250:1 to 1:1.

37. The process of claim 30 wherein the unresolved optical isomer of the alpha amino acid substituted at the carbonyl group is in a substantially anhydrous water-immiscible inert organic solvent and is racemized by heating the solution of said optical isomer in the inert substantially anhydrous water-immiscible organic solvent in combination with an effective amount of pyridoxal-5-phosphate to an effective temperature and for an effective period of time sufficient to racemize at least 10% of said isomer.

38. The process according to claim 1 wherein said optical isomer is a $C_1$–$C_8$ ester of an alpha amino acid.

39. The process according to claim 38 wherein the amino acid ester is an ester of phenylalanine.

40. The process according to claim 37 wherein the substantially anhydrous water-immiscible inert organic solvent is selected from the group consisting of toluene, methylene chloride, cyclohexanone, ethyl acetate, butyl acetate, butanol and mixtures thereof.

41. The process according to claim 37 wherein the pyridoxal-5-phosphate is immobilized.

42. The process according to claim 37 wherein said temperature ranges from about 50° C. to about 120° C.

43. The process according to claim 37 wherein the temperature is the reflux temperature of the solvent at atmospheric pressure.

* * * * *

UNITED STATES PATENT AND TRADEMARK OFFICE
CERTIFICATE OF CORRECTION

PATENT NO. : 4,613,691

DATED : September 23, 1986

INVENTOR(S) : Stanley B. Mirviss and Mark W. Empie

It is certified that error appears in the above—identified patent and that said Letters Patent is hereby corrected as shown below:

On the title page,

In Other Publications - Harn et al. "J. A. Swu Chem Soc" should be -- J. Am. Chem. Soc. --.

- Barrows, please insert 71 after Vol.

Col. 1, line 30 - "are" precursors should be -- as -- precursors.

Col. 2, line 27 - "Zinc" should be -- zinc --.

Col. 3, line 54 - "decarboxylic" should be -- dicarboxylic --.

Col. 4, line 66 - "names" should be -- means --.

Col. 5, line 1 - "hydrogentation" should be -- hydrogenation --.

Col. 5, line 17 - "hydroxyide" should be -- hydroxide --.

Col. 5, line 59 - "benzahydantoin" should be -- benzalhydantoin --.

Col. 8, line 27 - add the word "formed" after the word "salt".

Col. 9, line 47 - "sulution" should be -- solution --.

Col. 9, line 50 - "so formed" should be -- so-formed --.

UNITED STATES PATENT AND TRADEMARK OFFICE
CERTIFICATE OF CORRECTION

PATENT NO. : 4,613,691
DATED : September 23, 1986
INVENTOR(S) : Stanley B. Mirviss and Mark W. Empie It is certified that error appears in the above—identified patent and that said Letters Patent is hereby corrected as shown below:

Col. 9, line 55 - "otpical" should be -- optical --.

Col. 10, line 55 - "protease" should be -- proteases --.

Col. 10, line 62 - "excess" should be --excessive--.

Col. 12, line 3 - "equilibrum" should be -- equilibrium --.

Col. 16, line 21 - omit the word "ester" after "amino acid".

Col. 16, line 35 - insert the word -- at -- after the word "phosphate" and before the word "a".

Col. 23, line 42 - "was" should be -- were --.

Col. 23, line 53 - "phospate" should be -- phosphate --.

Col. 26, line 31, in Claim 23 - "19" should be -- 22 --.

Signed and Sealed this

Sixth Day of January, 1987

Attest:

DONALD J. QUIGG

Attesting Officer     Commissioner of Patents and Trademarks